United States Patent
Attar et al.

(10) Patent No.: US 9,044,258 B2
(45) Date of Patent: Jun. 2, 2015

(54) INSTRUMENT WITH REMOVABLE TIP

(75) Inventors: Matthew J. Attar, New Bedford, MA (US); Michael Jacene, Blackstone, MA (US); Jerry R. Griffiths, Pembroke, MA (US); Leo Gowin, Abington, MA (US); Christopher Johnson, Abington, MA (US); Louis J. Marini, Abington, MA (US)

(73) Assignee: Specialty Surgical Instrumentation Inc., Antioch, TN (US)

( * ) Notice: Subject to any disclaimer, the term of this patent is extended or adjusted under 35 U.S.C. 154(b) by 237 days.

(21) Appl. No.: 13/337,530

(22) Filed: Dec. 27, 2011

(65) Prior Publication Data

US 2013/0165907 A1 Jun. 27, 2013

(51) Int. Cl.
*A61B 17/29* (2006.01)
*A61B 17/3201* (2006.01)
*A61B 17/00* (2006.01)

(52) U.S. Cl.
CPC .............. *A61B 17/29* (2013.01); *A61B 17/3201* (2013.01); *A61B 2017/0023* (2013.01); *A61B 2017/00336* (2013.01); *A61B 2017/00473* (2013.01); *A61B 2017/2905* (2013.01); *A61B 2017/2931* (2013.01); *A61B 2017/2936* (2013.01)

(58) Field of Classification Search
CPC ............... A61B 17/29; A61B 17/3201; A61B 2017/00336; A61B 2017/00473; A61B 2017/2905; A61B 2017/2931; A61B 2017/2936

USPC .......................................................... 606/41
See application file for complete search history.

(56) References Cited

U.S. PATENT DOCUMENTS

| 5,368,600 | A | 11/1994 | Failla et al. | |
|---|---|---|---|---|
| 5,509,923 | A | 4/1996 | Middleman et al. | |
| 8,668,702 | B2 * | 3/2014 | Awtar et al. | 606/130 |
| 2003/0212435 | A1 * | 11/2003 | Gold et al. | 606/206 |
| 2011/0251606 | A1 * | 10/2011 | Kerr | 606/34 |
| 2013/0023911 | A1 * | 1/2013 | Esanu | 606/158 |

FOREIGN PATENT DOCUMENTS

| WO | 9915089 A1 | 4/1999 |
|---|---|---|
| WO | 2007142977 A2 | 12/2007 |
| WO | 2012126477 A1 | 9/2012 |

* cited by examiner

*Primary Examiner* — Aaron Roane
(74) *Attorney, Agent, or Firm* — Christopher & Weisberg, P.A.

(57) ABSTRACT

A laparoscopic instrument is disclosed, including an elongated tube defining a proximal portion and a distal portion; an end effector removably coupled to the distal portion, the end effector including first and second elements pivotably coupled to one another; an anchor coupled to the tube and a pivot point of the end effector to restrict axial movement of the end effector; and a sleeve movably coupled to the tube, where the sleeve is slidable across at least a portion of the end effector to secure the end effector to the tube.

6 Claims, 5 Drawing Sheets

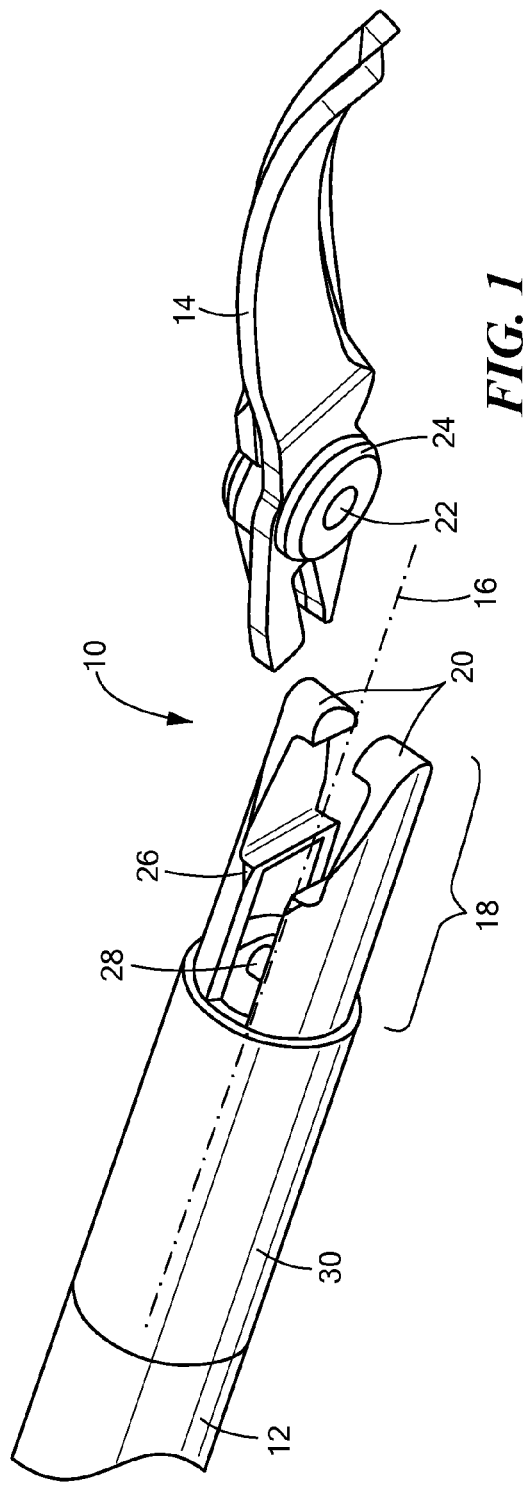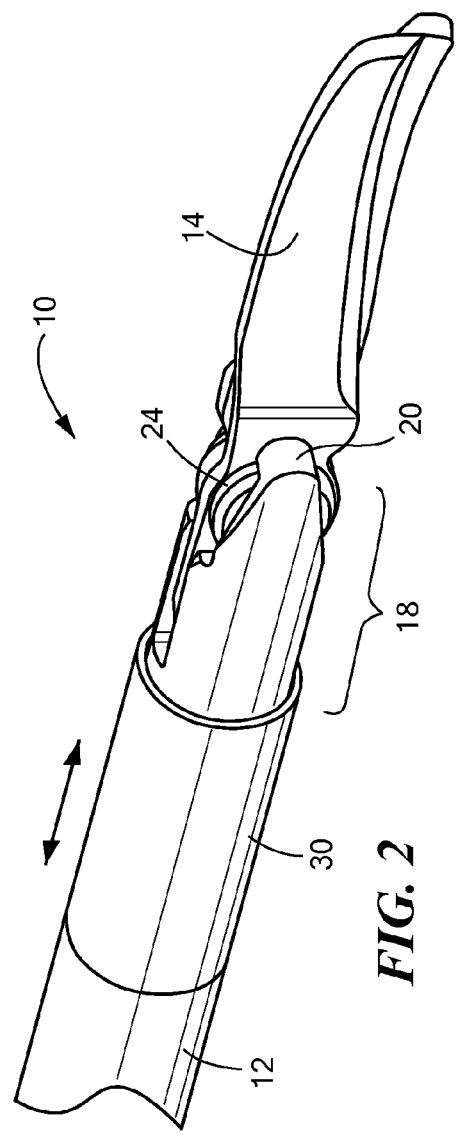

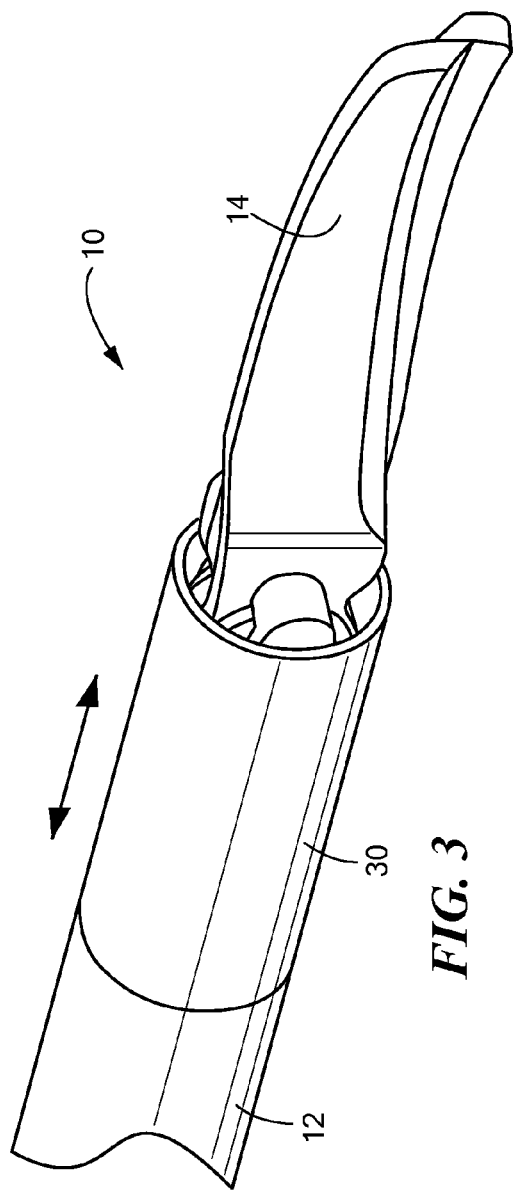
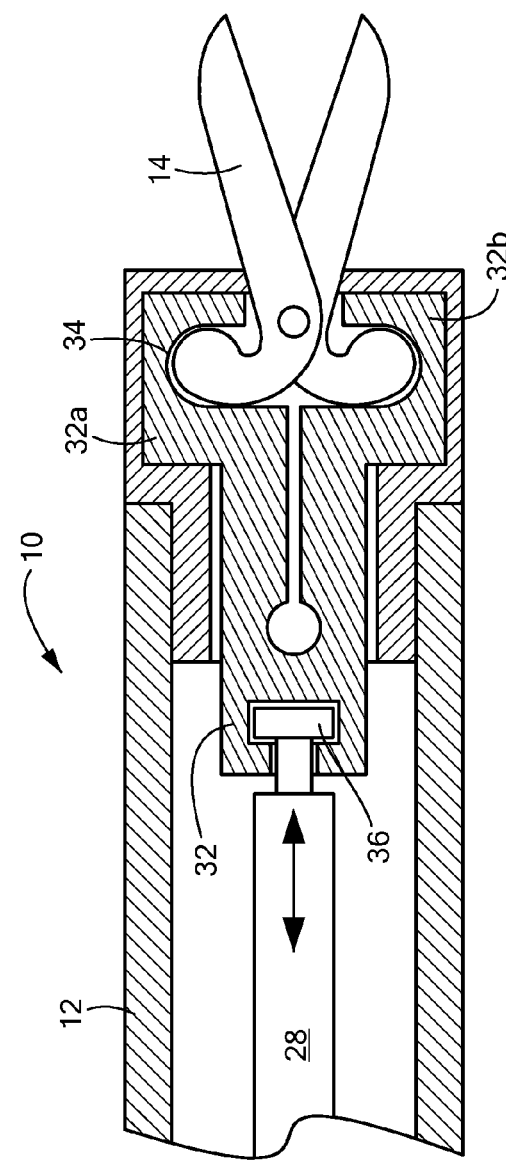

INSTRUMENT WITH REMOVABLE TIP

CROSS REFERENCE TO RELATED APPLICATION n/a

STATEMENT REGARDING FEDERALLY SPONSORED RESEARCH OR DEVELOPMENT n/a

FIELD OF THE INVENTION

The present invention relates generally to surgical instruments and methods of use, and more particularly to endoscopic or laparoscopic instruments and methods of use.

BACKGROUND OF THE INVENTION

Laparoscopic and endoscopic surgical procedures typically include routing a small device through a small incision in the skin or natural body orifices. To effectively operate in these small openings and associated regions, surgeons must use instruments that have a small enough cross section to ease insertion through the incisions as well as having sufficient length to reach the targeted or designated surgical area within the body. Endoscopic and laparoscopic instruments utilized for these procedures are often separated into two or more components to reduce costs and minimize cross contamination, where some of the components are disposable, one-time-use parts and the other components are sterilizable or otherwise available for repeated use.

For example, one component typically includes a long and narrow disposable portion that is inserted into the small opening during surgery. These disposable components may contain surgical tools, such as surgical jaws, clip-appliers, dissectors or other instruments on the end that enters the patient. These disposable components also typically contain small actuators which control the operation of the surgical tools within the patient. These small actuators are often operatively attached to another, non-disposable component of these surgical instruments. The non-disposable component may include a control unit for moving the disposable component within the patient and operating the disposable actuators during a particular procedure.

However, the inclusion of complex attachment mechanisms and actuators in the disposable components of a surgical instrument increases the costs incurred for each procedure. Moreover, existing attachment mechanisms coupling the disposable portions to the non-disposable components typically include helical threads, ball joins, and other mechanisms that can be difficult to disassemble for the disposal of the use components. Indeed, such couplings may require a physician or surgeon to grasp a sharp, pointed end effector of the device in order to twist and detach the disposable portion from the non-disposable portion, which can lead to unintended injury.

In view of the above, it is desirable to provide a laparoscopic assembly having complex control and actuation mechanisms in a re-usable handle while minimizing complexity and thus costs for disposable components of the device. It is further desirable to provide end effector assemblies that are readily detachable with minimal effort and reduced need for direct interaction with sharpened end effectors.

SUMMARY OF THE INVENTION

The present disclosure advantageously provides laparoscopic instruments and methods of use thereof having control and actuation mechanisms in a re-usable handle while minimizing complexity and thus costs for disposable distal components of the instruments, as well as providing end effector assemblies that are readily detachable with minimal effort and reduced need for direct interaction with sharpened or contaminated end effectors.

Particularly, a surgical instrument is provided, including a flexible body; an end effector removably coupled to the flexible body and extending past a distal end of the flexible body; and a sleeve movably coupled to the flexible body, where the sleeve is slidable from a first position that secures the end effector to the flexible body to a second position allowing disengagement of the end effector from the flexible body. The sleeve may extend around 360 degrees of at least a portion the end effector or extend around less than 360 degrees of at least a portion the end effector. The instrument may include an actuator at least partially disposed in the flexible body and releasably engageable with the end effector, where the actuator is operable to manipulate the end effector. The actuator may include a shaft movably disposed within the flexible body and/or the end effector may be rotatable around the actuator. The instrument may include an anchor coupled to the flexible body and releasably engageable with the end effector to restrict axial movement of the end effector. The anchor may include a pin passable through a pivot point defined by the end effector and/or a plurality of protrusions abutting a projecting surface defined by the end effector. The end effector may include a cutting element, a gripping element, a suturing element, or other diagnostic or treatment assemblies.

A laparoscopic instrument is provided, including an elongated tube defining a proximal portion and a distal portion; an end effector removably coupled to the distal portion, the end effector including first and second elements pivotably coupled to one another; an anchor coupled to the tube and a pivot point of the end effector to restrict axial movement of the end effector; and a sleeve movably coupled to the tube, where the sleeve is slidable across at least a portion of the end effector to secure the end effector to the tube. The anchor may include a pin passable through the pivot point and/or a plurality of protrusions abutting a projecting surface proximate the pivot point. The instrument may include an actuator at least partially disposed in the tube and releasably engageable with the end effector, wherein the actuator is operable to manipulate the end effector. The actuator may include a shaft movably disposed within the flexible body and a flexible link receiving at least a portion of the end effector therein.

A method of coupling an end effector to a laparoscopic instrument is provided, including releasably coupling a pivot point of the end effector to an elongated, flexible body such that axial movement of the end effector is substantially inhibited; and sliding a sleeve across at least a portion of the end effector to secure the end effector to the flexible body. Releasably coupling the pivot point of the end effector to the flexible body may include passing a pin anchored to the flexible body through the pivot point and/or positioning a projecting surface of the pivot point proximal to a plurality of distally-extending anchors attached to the flexible body. The method may include releasably engaging an actuator to the end effector, where the actuator is operable to manipulate the end effector. The sleeve may extend around less than 360 degrees of at least a portion the end effector.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is an illustration of an example of a surgical or laparoscopic instrument constructed in accordance with the principles of the present disclosure;

FIG. 2 is another illustration of the laparoscopic instrument of FIG. 1;

FIG. 3 is yet another illustration of the laparoscopic instrument of FIG. 1;

FIG. 4 is an illustration of a first side view of another example of a laparoscopic instrument constructed in accordance with the principles of the present disclosure;

DETAILED DESCRIPTION OF THE INVENTION

Figure 5:
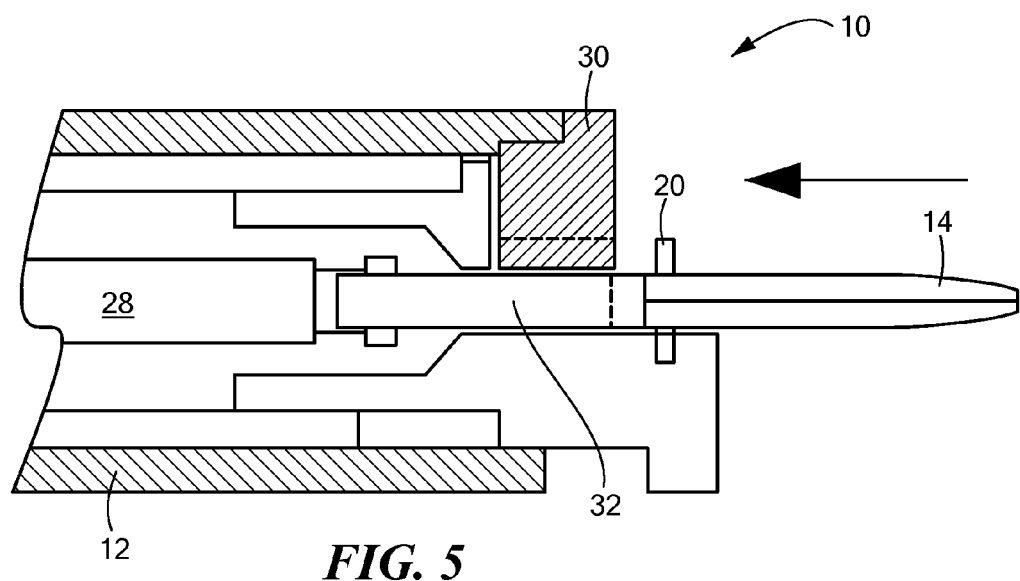
FIG. 5 is an illustration of another side view of the laparoscopic instrument of FIG. 4.

The present disclosure advantageously provides laparoscopic instruments and methods of use thereof having control and actuation mechanisms in a re-usable handle while minimizing complexity and thus costs for disposable distal components of the instruments, as well as providing end effector assemblies that are readily detachable with minimal effort and reduced need for direct interaction with sharpened or contaminated end effectors. Now referring to the figures in which like reference designators refer to like elements, there is shown in FIG. 1 an exemplary surgical instrument designated generally as "10." The instrument 10 may include, for example, an endoscopic and/or laparoscopic instrument positionable or passable through an incision and directable towards a tissue site or region selected for diagnosis, treatment, or other action facilitated by the instrument 10.

The instrument 10 generally includes an elongated flexible body or tube 12 that can be at least partially positioned within a patient. The flexible body 12 may define one or more lumens therethrough for the passage or housing of one or more internal components of the instrument 10, such as one or more steering elements, sensors, control mechanisms, or the like that enable operation and manipulation of components located at a distal portion of the instrument 10 by controls or actuators at a proximal portion of the device. Of note, as used herein, the term "proximal" is intended to mean closer to or in proximity to a surgeon or user-accessible portion of the instrument 10, while "distal" is intended to mean closer to or in proximity to a portion of the instrument 10 closer to a tissue site to be treated or operated upon. The elongated flexible body 12 of the instrument 10 may include sufficient length to traverse an anatomical path from an incision or orifice in a patient to a particular surgical site within the body 12.

The instrument 10 may also include one or more end effectors 14 at a distal portion of the device that facilitate diagnosis, treatment, removal, repair or other action performed with respect to the targeted tissue site. For example, the end effector(s) may include one or more cutting elements or instruments, tissue gripping or clamping components, suturing mechanisms, energy-delivery components (such as radiofrequency, microwave, laser or other energy modalities), or the like. In the particular examples illustrated in FIGS. 1-8, the end effectors 14 include two blades or cutting elements in a scissor configuration that extend beyond a distal end of the flexible body 12. The blades constituting the illustrated end effectors 14 are pivotably coupled to one other to provide the operable opening and closing of the blades to excise tissue.

The end effectors 14 may be selectively and removably coupled to the distal portion of the elongate body 12. The readily-disengaged coupling between the end effectors 14 and the body 12 allows a surgeon to quickly remove and dispose a used end effector while sterilizing the remaining components of the instrument 10 for re-use. Alternatively, a surgeon or end-user may readily replace one end effector with another to perform different tasks or actions in a single procedure. In particularly, the end effectors 14 may be releasably engaged to the flexible body 12 such that the end effectors 14 are axially secured or otherwise substantially inhibited from uncontrolled longitudinal movement along an axis 16 of the body 12, while retaining operability of the end effectors 14 and/or a rotational range of motion of the end effectors 14 with respect to the flexible body 12.

For example, now referring to FIGS. 1-3, the end effectors 14 may be inserted "downward" into a retaining structure or segment 18 of the instrument 10 extend form or coupled to the flexible body 12. Of note, to the extent used herein, the terms "downward," "top," "bottom" or "side" are intended only to provide a frame of reference for ease of explanation, and are not intended as an absolute reference or limiting description of the direction or orientation of the respective components or features of the described examples. The instrument 10 may include one or more anchors 20 that engage or otherwise receive a portion of the end effectors 14 to restrain unwanted axial movement along the flexible body 12. For example, as shown in FIGS. 1-2, the anchor 20 includes two projecting arms that extend inward substantially perpendicularly to a longitudinal axis of the flexible body 12. The anchors 20 abut or otherwise align distally to an adjacent surface on the end effectors 14, which may be defined by a pivot point or joint 22 of the end effectors 14. For example, as shown in FIG. 1, the end effectors 14 may be pivotably connected to one another through a rivet or cap 24 circumscribing or surrounding the pivot point 22. The rivet 24 defines a projecting surface or side wall positionable proximally to the anchors 20. The anchors 20 thus prevent distal movement of the end effectors 14 once in position, as shown in FIG. 2. The instrument 10 may further include one or more retention features or anchors preventing proximal movement of the end effectors 14 when coupled to the flexible body 12. For example, as shown in FIG. 1, one or more projecting sidewalls 26 may extend from the flexible body 12 to abut or adjacently align with a proximal surface or sidewall of the rivet 24 of the end effectors 14.

The instrument 10 may include one or more actuators or actuating elements 28 at least partially disposed within the flexible body 12 and releasably engageable with the end effector such that operation or manipulation of the actuator 28 results in operation or manipulation of the end effector. The actuator(s) may include, for example, one or more pull wires, torqueable bodies, or other mechanical, electrical, or other mechanisms or assemblies extending through the length of the flexible body 12 that are accessible or operable from a proximal end or portion of the instrument 10. For example, as shown in FIG. 1, the actuator 28 may include a transverse pin engageable with a slot or other complementary feature of the end effectors 14, where movement of the transverse pin results in opening or closing of the end effectors 14.

The instrument 10 may further include a sleeve or sheath 30 movably coupled to the flexible body 12 to secure the end effector(s) 14 into place at the distal portion or retaining segment of the instrument 10. The sleeve 30 may include a cylindrical body 12 that surrounds at least a portion of the flexible body 12 and can be controllably and selectively transitioned from a first position or configuration allowing engagement or disengagement of the end effector from the flexible body 12 (as shown in FIGS. 1-2, for example) to a second configuration or position that secures the end effector to the flexible body 12 (as shown in FIG. 3, for example). The first position may include movement of the sleeve 30 in a proximal direction providing access to the retaining segment 18 of the instrument 10, while the second position may include sliding or moving the sleeve 30 distally to cover or surround at least a portion of the retaining segment 18 and/or the end effectors 14 to prevent unwanted or unintended disengagement. The sleeve 30 may be manually slidable through direct interaction with the sleeve 30 and/or distal portion of the flexible body 12. Alternatively, movement of the sleeve 30 may be accomplished using one or more steering or pulling wires traversing at least a portion of the flexible body 12.

Figure 6:
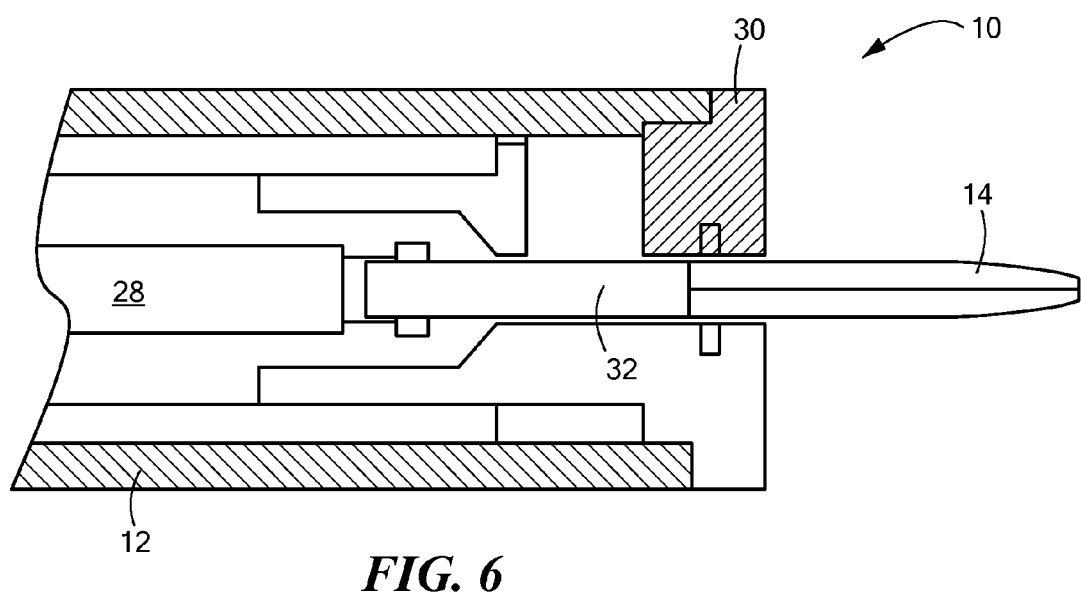
FIG. 6 is yet another illustration of the laparoscopic instrument of FIG. 4.

Now referring to FIGS. 4-6, an alternative example of the instrument 10 is illustrated. In this exemplary configuration, the end effector 14 may be positioned laterally or "side loaded" into a cavity or pocket coupled to or defined by the distal portion of the flexible body 12. For example, the instrument 10 may include a linking element 32 that defines a cavity 34 sized and/or shaped to accommodate or receive a proximal portion of the end effectors 14. The linking element 32 may be constructed from a flexible material to allow some displacement, flexing, or movement of the end effectors 14 to a desired degree. The linking element 32 may include two separated portions 32a, 32b having a space therebetween to form a joint or other pliable construct to impart the desired flexibility of the linking element.

The linking element 32 may further couple to the actuator 28 such that the linking element (and the end effectors 14) is rotatable about the actuator 28. For example, the actuator 28 may include an elongated shaft having a rounded or cylindrical end 36 that matably couples to a complementary opening in the linking element 32. This configuration allows axial movement of the actuator 28 to impart operation or manipulation of the end effectors 14, while allowing the end effectors 14 to rotate or pivot freely about the actuator 28 in tortuous anatomical environments or passages.

Continuing to refer to FIGS. 4-6, the retaining segment 18 of the instrument 10 may include the anchor 20 in the form of a pin or protruding rod that passes through a pivot joint or point 22 of the end effectors 14. Once the end effectors 14 are positioned onto the anchor 20, the axial movement of the end effectors 14 is restrained, while axial movement or forces imparted onto the end effectors 14 through the linking element 32 result in the opening and closing of the end effectors 14.

Now referring to FIGS. 5-6, the instrument 10 includes the sleeve 30 that is movably positionable to either allow engagement/disengagement of the end effectors 14 to the flexible body 12 or secure the end effectors 14 into place. In this particular example, the sleeve 30 extends around a portion of the circumference of the flexible body 12, e.g., less than 360 degrees. The sleeve 30 is positionable to expose a side of the cavity 34 in the linking element 32 and the anchor 20 for receiving or attaching the end effectors 14 (as shown in FIG. 5), while also being slidably positionable in a second position to cover an otherwise exposed side of the end effectors 14 and/or linking element 32 (as shown in FIG. 6), thereby securing the end effectors 14 into position on the flexible body 12 for use.

Figure 7:
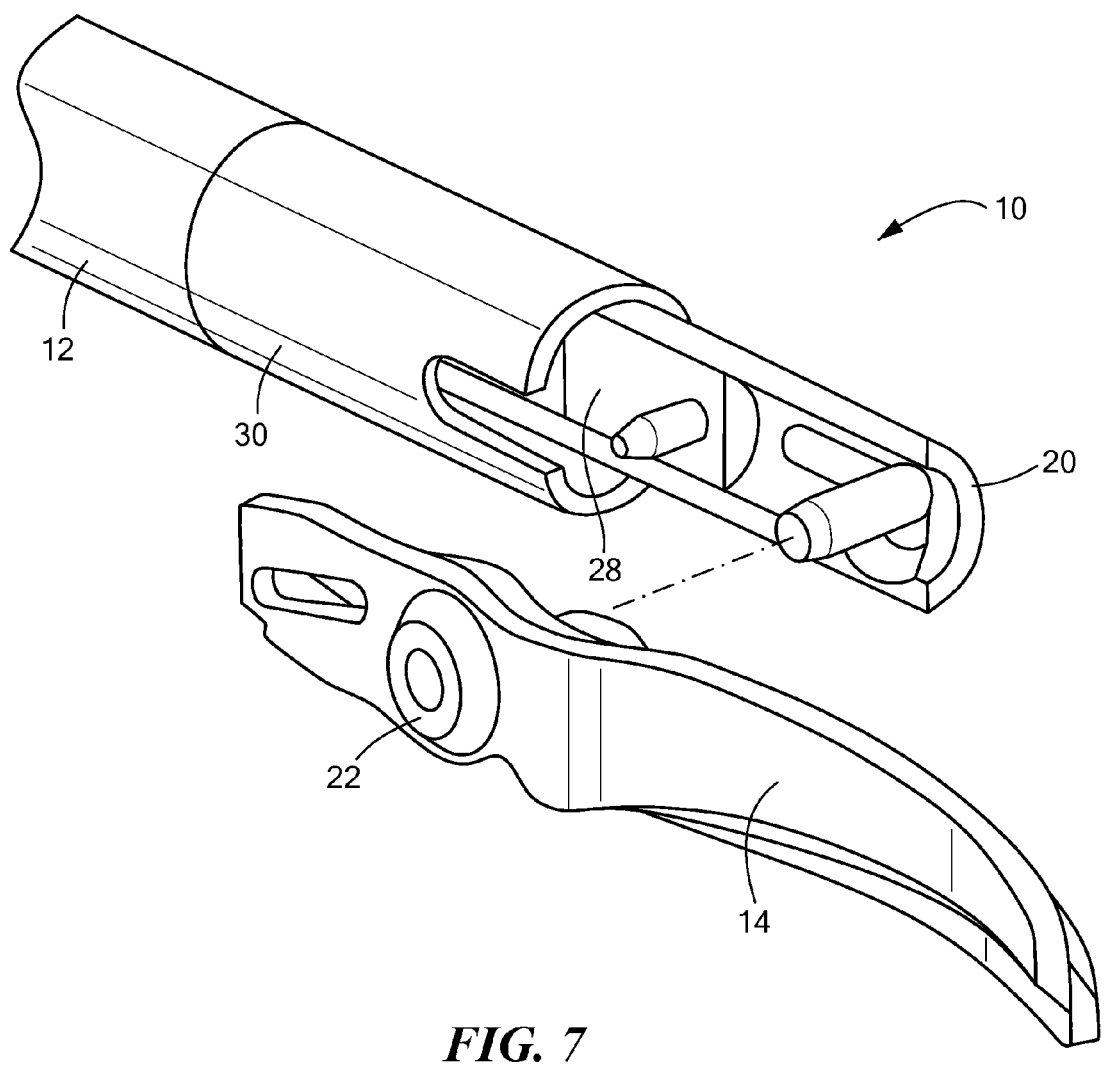
FIG. 7 is an illustration of an example of a laparoscopic instrument constructed in accordance with the principles of the present disclosure.
Figure 8:
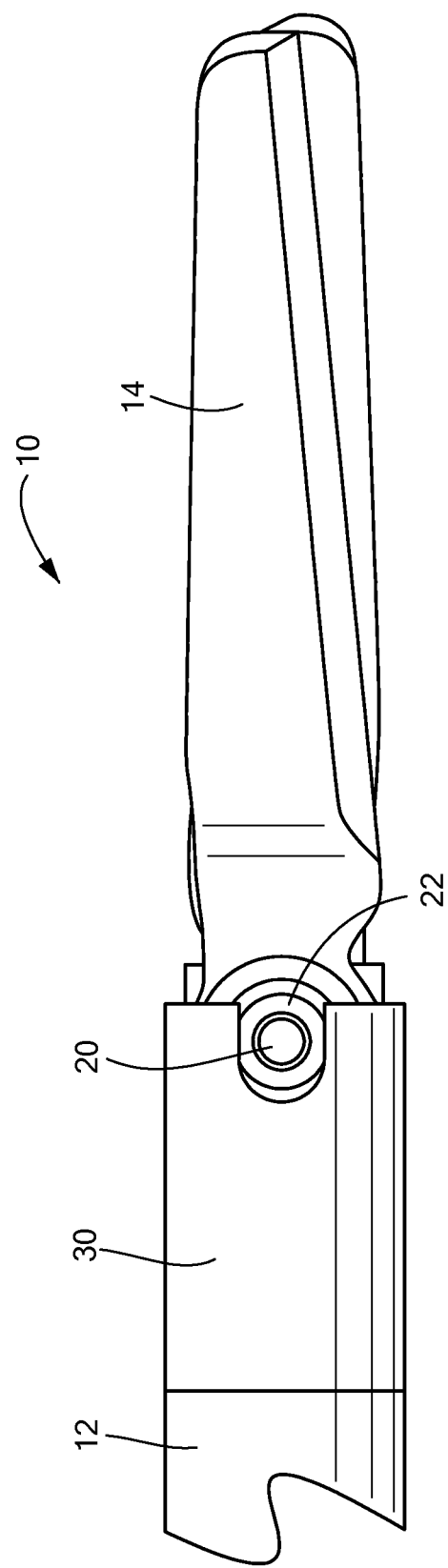
FIG. 8 is another illustration of the laparoscopic instrument of FIG. 7.

Now referring to FIGS. 7-8, an additional example of the instrument 10 is illustrated. In this exemplary configuration, the end effectors 14 may be laterally engaged with an anchor 20 and actuator 28 extending from the retaining segment of the instrument 10. For example, the actuator 28 may include a transverse pin engageable with a slot or other complementary feature of the end effectors 14, where movement of the transverse pin results in opening or closing of the end effectors 14. The pin may be coupled to an elongated segment extending distally on one side of the instrument 10. In addition, the retaining segment 18 of the instrument 10 may include the anchor 20 in the form of a pin or protruding rod similarly coupled to the elongated segment extending distally on one side of the instrument 10. The anchor 20 passes through a pivot joint or point 22 of the end effectors 14, allowing relative pivotal motion between the two blades of the end effectors 14. Once the end effectors 14 are positioned onto the anchor 20, the axial movement of the end effectors 14 is restrained, while axial movement or forces imparted onto the end effectors 14 through the linking element again result in the opening and closing (or other operation) of the end effectors 14.

The instrument 10 again includes the sleeve 30 that is movably positionable to either allow engagement/disengagement of the end effectors 14 to the flexible body 12 or secure the end effectors 14 into place. In this particular example, the sleeve 30 is positionable to expose the protruding anchor and actuator 28 (as shown in FIG. 7), while also being slidably positionable in a second position to cover a portion of the end effectors 14, the actuator 28, and/or the anchor 20 (as shown in FIG. 8), thereby securing the end effectors 14 into position on the flexible body 12 for use.

In an exemplary method of securing or releasing a detachable end effector from a flexible body 12 or main shaft of the instrument 10, the end effector 14 is releasably coupled to an at the distal portion of the flexible body 12 such that unintended axial movement of the end effectors 14 is restrained or altogether inhibited. This may be achieved by engaging the anchor 20 to the end effectors 14, which may include passing the anchor 20 through a pivot point or joint 22 of the end effectors 14, which still allows operation (e.g., opening and closing) of the end effectors 14. The releasable coupling of the end effectors 14 to the flexible body 12 may further include engaging an actuator 28 to the end effectors 14, which allows operation of the effectors 14 remotely (i.e., form a proximal portion of the instrument 10). Once axial movement has been restrained, operational coupling to the actuator 28 has been confirmed, and/or the end effectors 14 are otherwise in suitable position on or about the flexible body 12, the sleeve 30 may be transitioned to at least partially cover one or more of the anchor 20, actuator 28, and or end effectors 14 to secure the components in place for subsequent use. For subsequent removal or disengagement of the end effectors 14, the sleeve 30 may be retracted, allowing the end effectors 14 to be removed from the anchor and/or actuator. This may be achieved, for example, by simply tapping the distal portion of the flexible body 12, thereby reducing the likelihood of any unintended injury or unnecessary handling of sharp edges of a particular end effector.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A surgical instrument, comprising:
   a flexible tubular body;
   an end effector removably coupled to the flexible body and extending past a distal end of the flexible body, wherein the end effector comprises opposing jaw members pivotably connected;
   a sleeve movably coupled to and circumscribing at least a portion of the flexible tubular body, the sleeve being slidable from a first position that secures the end effector to the flexible tubular body to a second position allowing disengagement of the end effector from the flexible tubular body; and
   an anchor coupled to and extending beyond the distal end of the flexible tubular body, the anchor being releasably engageable with the end effector, the opposing jaw members being pivotably connected to one another through a rivet and a cap surrounding the pivot point to restrict axial movement of the end effector, the anchor including a plurality of protrusions abutting a projecting surface defined by the end effector.

2. The instrument of claim 1, wherein the sleeve extends around 360 degrees of at least a portion the end effector.

3. The instrument of claim 1, further comprising an actuator at least partially disposed in the flexible body and releasably engageable with the end effector, wherein the actuator is operable to manipulate the end effector.

4. The instrument of claim 1, wherein the end effector includes a cutting element.

5. A laparoscopic instrument, comprising:
   an elongated tube defining a proximal portion and a distal portion;
   an end effector removably coupled to the distal portion, the end effector including first and second elements pivotably coupled to one another;
   an anchor coupled to and extending beyond the distal end of the tube, the anchor being coupled to a cap surrounding a pivot point of the end effector, wherein the first and second elements are pivotably connected to one another through the rivet and the cap, the anchor being configured to restrict axial movement of the end effector; and
   a sleeve movably coupled to and circumscribing the tube, wherein the sleeve is slidable across at least a portion of the end effector to secure the end effector to the tube.

6. The instrument of claim 5, further comprising an actuator at least partially disposed in the tube and releasably engageable with the end effector, wherein the actuator is operable to manipulate the end effector.

* * * * *